United States Patent [19]

Polyakov et al.

[11] Patent Number: 5,437,602
[45] Date of Patent: Aug. 1, 1995

[54] ISOLATOR BAG FOR THERAPEUTIC TREATMENTS OF HUMAN LIMBS

[75] Inventors: Gregory M. Polyakov, Richmond; James I. Symons, New Westminster; Allen I. Bain; Michael J. A. Walker, both of Vancouver, all of Canada

[73] Assignee: ATM Wound Management, Inc., Vancouver, Canada

[21] Appl. No.: 107,324

[22] Filed: Aug. 13, 1993

[51] Int. Cl.6 .............................................. A61B 19/08
[52] U.S. Cl. ..................................... 600/21; 128/849; 128/856; 128/DIG. 24; 602/62
[58] Field of Search ................................. 128/849–856, 128/878, 882, 202.12, 205.26, DIG. 24; 604/304–307; 600/21; 5/423; 602/62

[56] References Cited

U.S. PATENT DOCUMENTS

| | | | |
|---|---|---|---|
| 3,850,172 | 11/1974 | Cazalis | 600/21 |
| 4,367,728 | 1/1983 | Muthe. | |
| 4,971,047 | 11/1990 | Kangler et al. . | |
| 5,029,579 | 7/1991 | Trammell | 128/205.26 |
| 5,178,162 | 1/1993 | Bose | 128/849 |
| 5,312,385 | 5/1994 | Greco | 604/356 |

Primary Examiner—Robert A. Hafer
Assistant Examiner—Michael O'Neill
Attorney, Agent, or Firm—Seed and Berry

[57] ABSTRACT

A flexible isolator bag used to isolate a controlled therapeutic gas atmosphere about a human limb for the management and treatment of wounds and lesions, or an amputation, has a discharge port and a flexible manifold section providing an intake manifold which has an infeed port and inlet openings to the interior of the bag. A self-sealing zipper extends along part of the length of the bag. The bag is secured to the patient by adhesive tape applied to the rim of the open end of the bag. This rim is shaped to prevent a tourniquet effect.

14 Claims, 5 Drawing Sheets

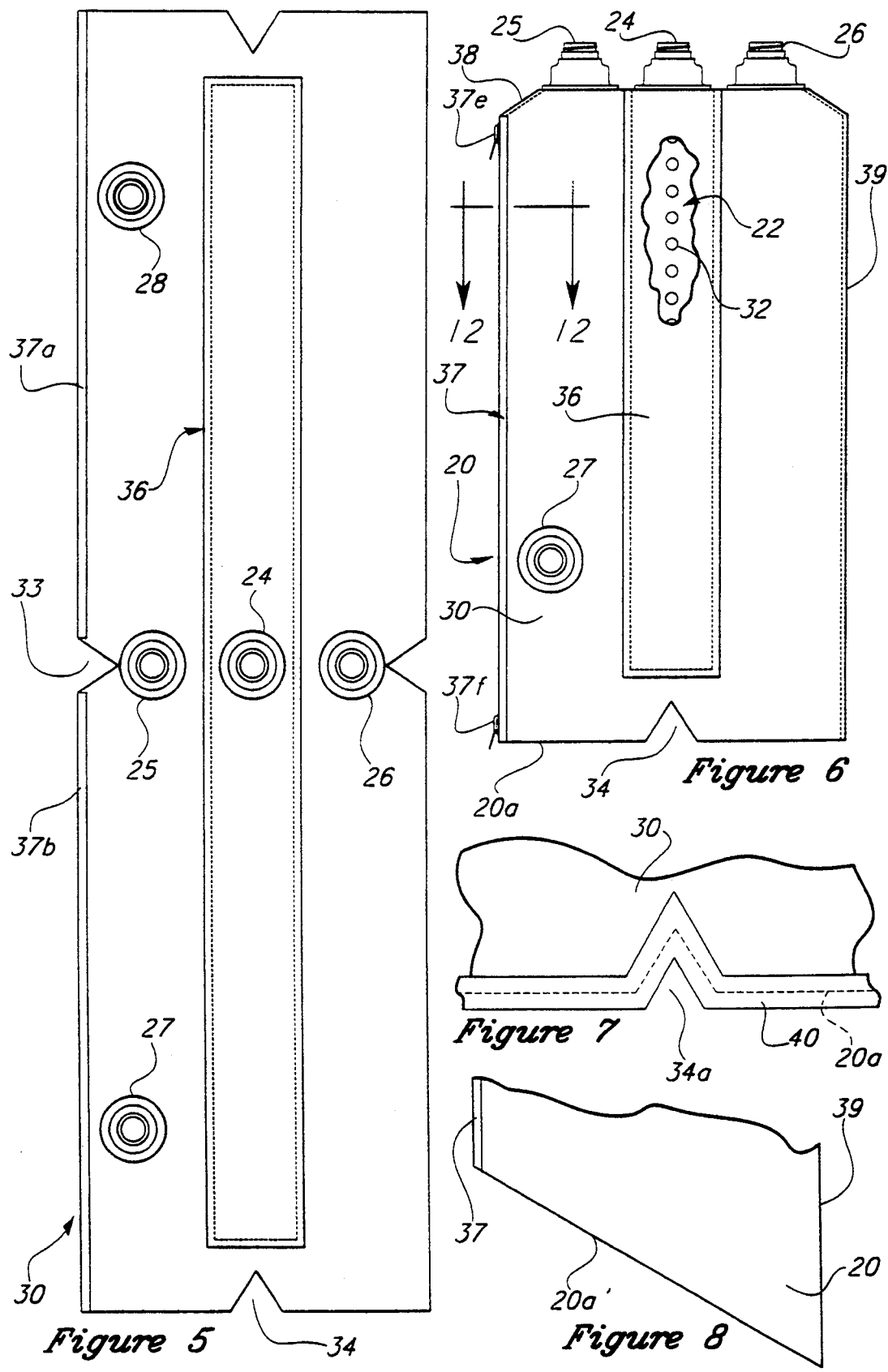

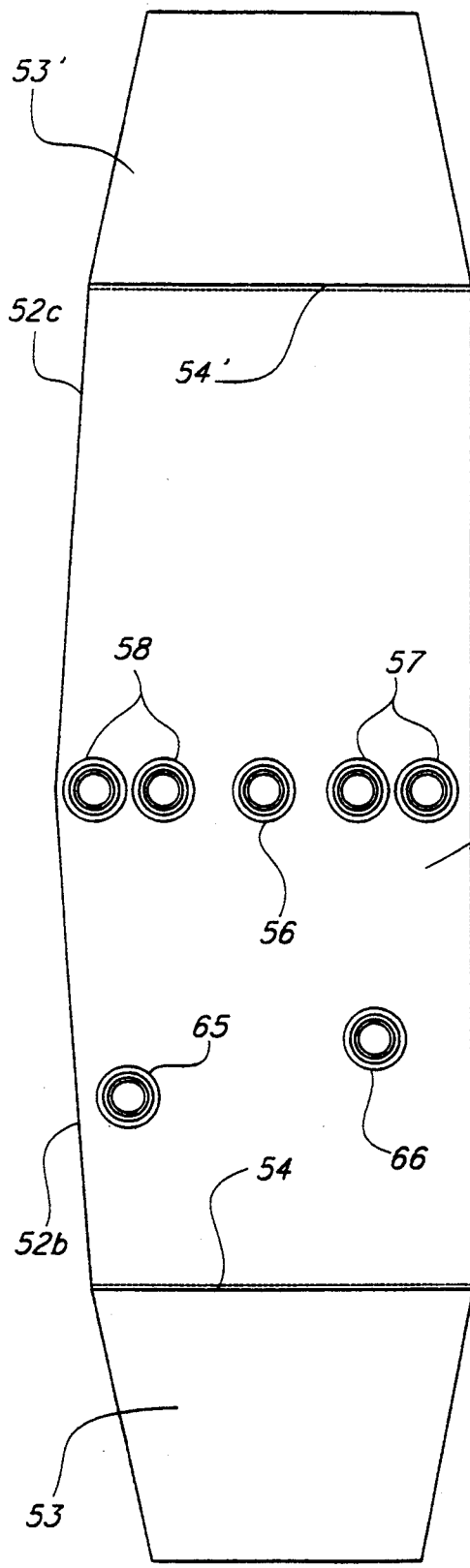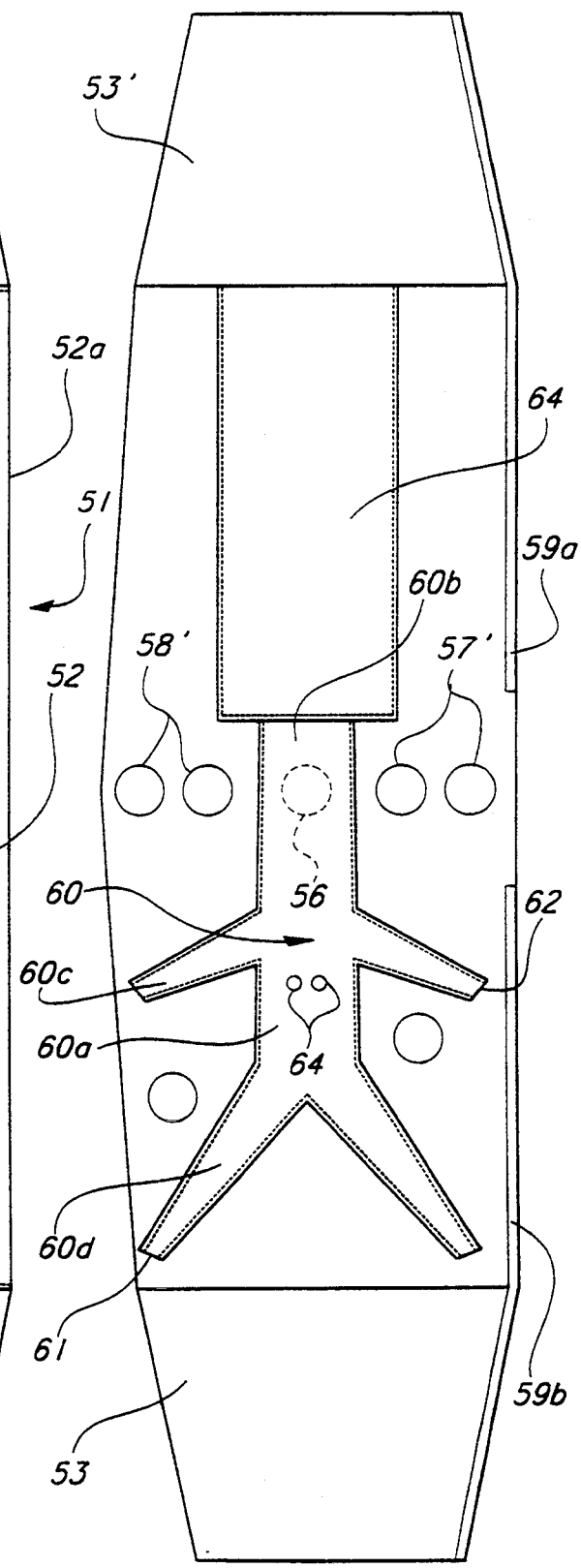

ISOLATOR BAG FOR THERAPEUTIC TREATMENTS OF HUMAN LIMBS

TECHNICAL FIELD

The present invention relates to isolator bags of the type used to isolate a controlled therapeutic gas atmosphere about a human limb for the management and treatment of wounds and lesions on the limb or an amputation.

BACKGROUND OF THE INVENTION

It has been recognized that treatment of burns and other lesions and wounds is enhanced by isolating the affected area and treating it with oxygen or other therapeutic gases in a controlled manner. When the affected area is on a limb, efforts have been made to provide a sealed treatment chamber about the limb by a flexible bag having its closed end at the extremity end of the limb, and its open end secured to an intact skin area near the opposite end of the limb as to provide a hermetic seal. The most common method of gas delivery into the bag chamber has been through a centrally located inlet port, but this can result in a concentration of therapeutic effect in one area and too little in other areas. This is frequently most evident during gas heating or chilling treatment modes. Prior art devices have generally attempted to solve this problem by employing a variety of throttling or flow metering methods. However these methods have not solved the basic problems of unequal temperature distribution along the limb surface, stagnant air pockets adjacent the bag extremities, and stagnant pockets of high relative humidity gas which promote the growth of certain microbes requiring the operators to somehow clean the interior surface of the bag or replace the bag.

Those isolator bag systems which introduce therapeutic gases at more than one inlet rely upon special external arrangements of tubes and valves creating gas flow patterns which are unduly complex and cause problems with gas flow regulation. Most often the prior art devices have included a rigid frame or support arm which not only is an additional weight for the patient to bear, but also creates an intrusive structure at the bed site.

Prior isolator bags, when sealed to the patient's limb, have been attached to the skin at or near 90° to the length of the limb. The resulting circumferential compression is likely to have a tourniquet effect causing compression of a vascular bundle, thereby impeding venous, lymphatic or arterial flow.

Previous isolator bags have been relatively difficult to install without contacting the affected areas and causing discomfort to the patient.

SUMMARY OF THE INVENTION

In view of the foregoing shortcomings of the prior art, the present invention provides an improved manifold system for isolator bags extending lengthwise of the bags and presenting multiple inlets by way of holes, slits or jets. The manifold is formed by bonding a manifold section of plastic film along its periphery to a plastic bag and connecting the resulting manifold area between the manifold section and the bag to a port fitting. The connection between the manifold section and bag are made while the bag is in the form of a plastic film blank, preferably polyvinylchloride (PVC). When the multiple inlets are in the form of holes or slits the manifold section can be secured on either the inside or outside of the bag; when outside, the inlet holes or slits are in the bag, and when inside, the inlet holes or slits are in the manifold. The number, spatial distribution, size and shape of the holes or slits can be adjusted to provide even gas flow and turbulence throughout the bag, or to provide increased flow in specific regions. When the air inlets are in the form of jets the manifold section is secured to the inside of the bag, and the jet inlets are provided at the extremities of tapered branches of the main body of the manifold section.

Prevention of a tourniquet effect is accomplished by sloping the rim at the open end of the bag from about 45° to 70° relative to the length of the bag, and/or by notching the rim and taping the rim to the patient by following the notched profile of the rim so as to prevent taping in a totally circumferential path.

The isolator bag is preferably fitted with a longitudinal plastic airtight zipper, opened from either end, which eases application of the bag on the patient and allows later access by nursing or medical staff to the affected area without necessitating removal of the bag.

In accordance with the invention the isolator bag may be formed with a frustoconical limb entry section which can later be shortened by trimming to enlarge the entry opening to accommodate various limb diameters, and which can be cut at an angle or notched to prevent a tourniquet effect as previously discussed.

BRIEF DESCRIPTION OF THE DRAWINGS

FIG. 5 is a plan view of the blanks after being connected together;

FIG. 6 is a plan view of the completed bag unit.

FIG. 7 is a fragmentary plan view showing taping of the bag unit;

FIG. 8 is a fragmentary plan view showing an alternative configuration for the open end of the bag unit;

FIG. 9 is a plan view of the bag blank for a second embodiment with port fittings in place;

FIG. 10 is a plan view of the bag blank for the second embodiment after application of the manifold section and other parts;

DETAILED DESCRIPTION OF THE INVENTION

Figure 12:
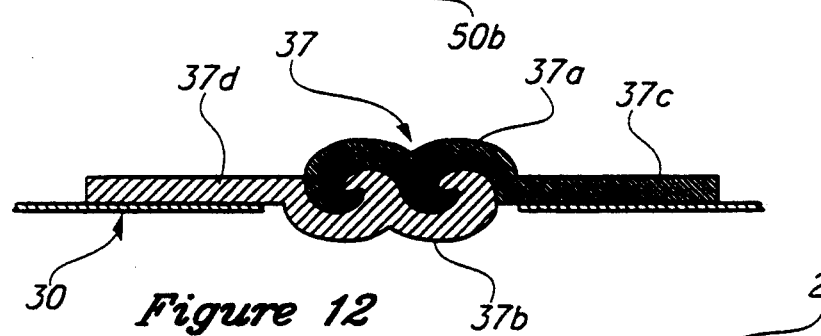
FIG. 12 is a cross-section of the zipper taken as indicated by line 12—12 of FIG. 6.
Figure 13:
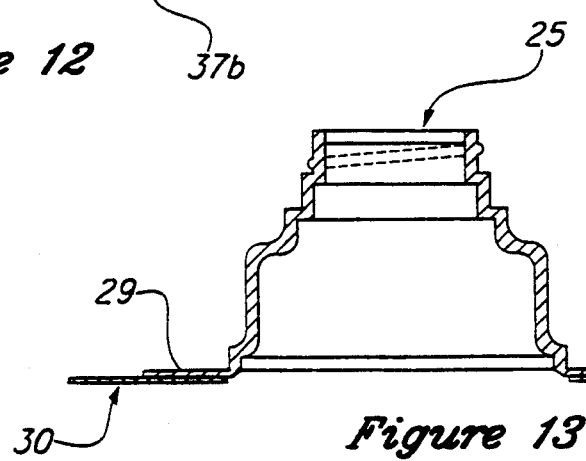
FIG. 13 is an elevational view of a port fitting taken as indicated by line 13—13 of FIG. 3.

The isolator bags of the present invention are preferably fabricated from flexible PVC fabric of about 0.008 to 0.010 inches thickness. This material is easily welded to itself by standard heat application or radio frequency welding techniques. Used in conjunction with the PVC fabric are PVC zipper fasteners (FIG. 12) and one-piece molded PVC port fittings (FIG. 13) having threaded nipples and mounting flanges which can be lap welded to the rim portion of port openings. The PVC zipper fasteners may be of 2-track construction and may be Minigrip, reclosable units marketed by ITW Minigrip Inc., Orangeburg, N.Y. Such units have flexible tracks which are interfitted and released by operation of a slider. The tracks extend laterally from mounting strips which can be lap welded to edge portions of the PVC fabric. Preferably the zippers are of the type having dual sliders permitting the zipper to be selectively opened from either end.

Figure 1:
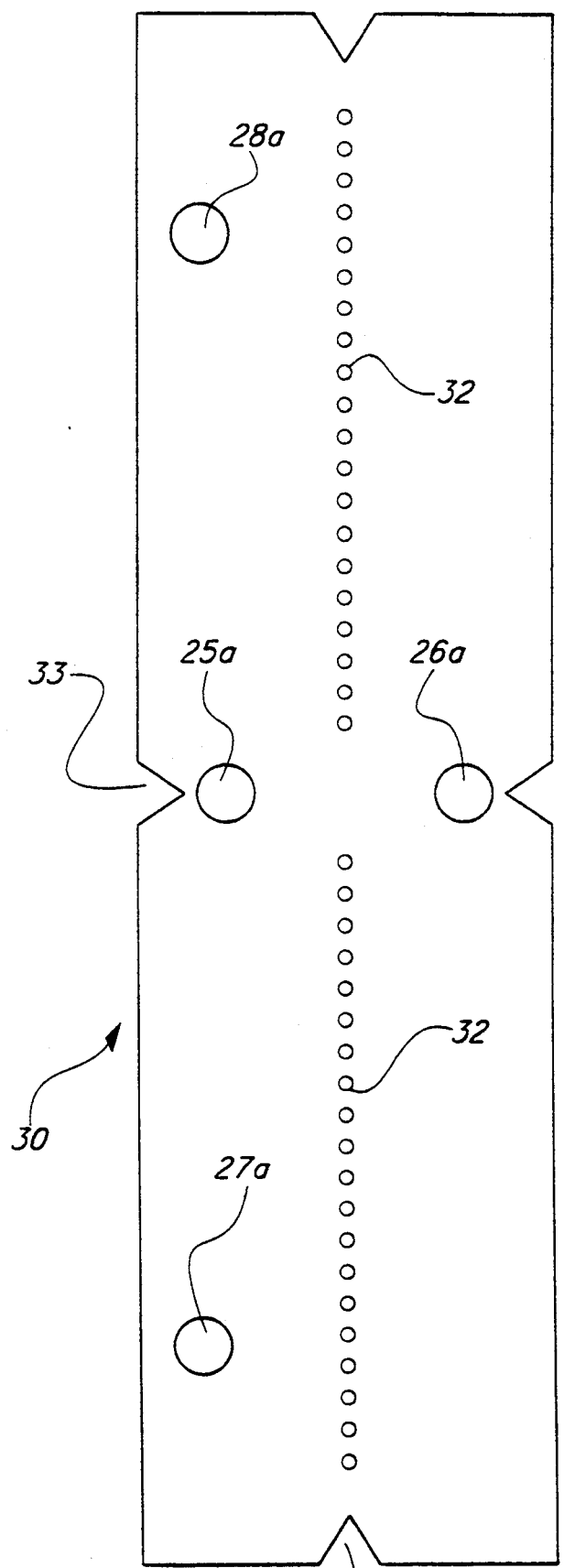
FIGS. 1 and 2 are plan views of bag and manifold blanks for making a first embodiment of the invention.
Figure 2:
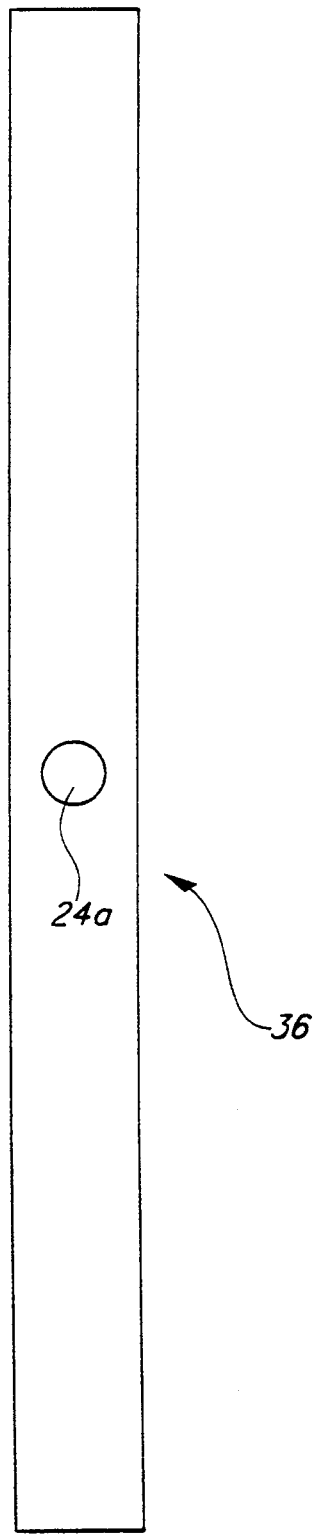
Figure 3:
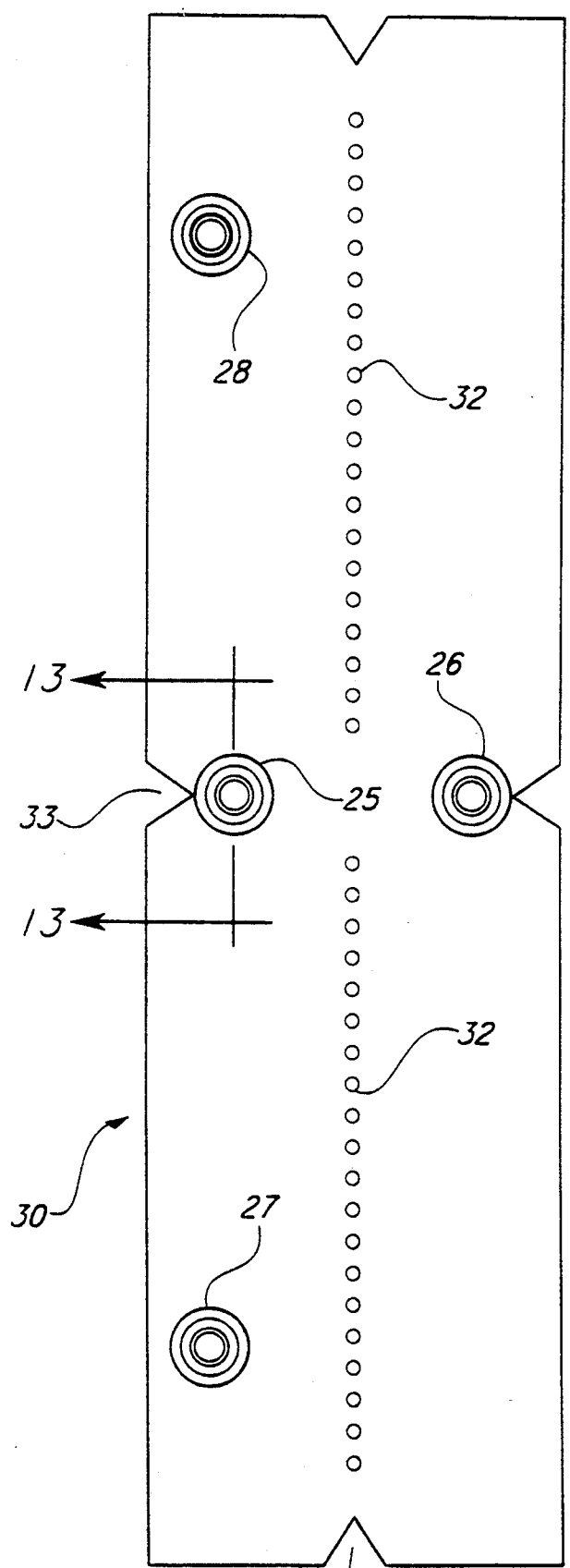
FIGS. 3 and 4 show the bag and manifold blanks after application of port fittings.
Figure 4:
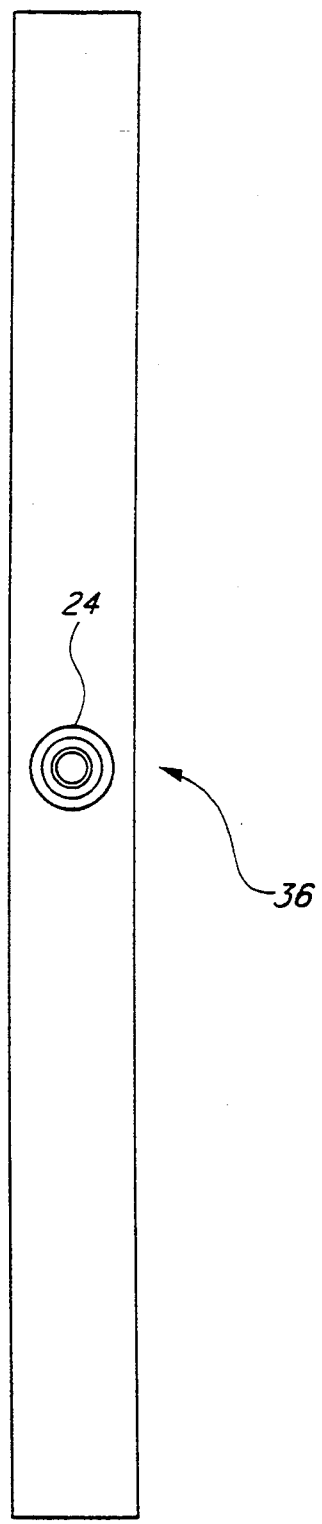

In a first embodiment of the invention (FIG. 6), a bag 20 has a center manifold 22 fed from a supply port 24, discharge ports 25-26, and access ports 27-28. The bag may be fabricated as indicated in FIGS. 1-5. A generally rectangular fabric bag blank 30 is formed along its longitudinal center line with two aligned rows of entry holes 32, two central discharge port holes 25a, 26a and two access port hole 27a-28a. The blank 30 may also be formed with central border cutouts 33 and one or more vee-shaped end notches 34. This blank 30 is complemented by a generally rectangular manifold blank 36 formed with a central supply port hole 24a. Next annular mounting flanges 29 on the port fittings 24-28 are welded to the rim portions of the port holes 24a-28a. The blanks are then as indicated in FIGS. 3-4. Continuing to FIG. 5, the manifold blank 36 is centered over the bag blank 30 and welded thereto along the periphery of the manifold blank. Complementing zipper tracks 37a, 37b of a zipper 37 have mounting flanges 37c, 37d which are welded in position along one longitudinal side edge of the bag blank on opposite sides of the respective cutout 33. Construction of the bag is completed by folding the combined bag/manifold blank in half and welding meeting edge portions together at seam 38 endwise of the zipper tracks and at seam 39 along the opposite longitudinal edge of the folded bag blank. Dual sliders 37e, 37f are provided for interfitting the zipper tracks so that the zipper 37 can be opened from either end. The bag unit is then as shown in FIG. 6.

For leg application the bag unit 20 may, for example, have a length and width of 55 inches by 22 inches for large legs, 44 by 19 inches for medium sized legs, and 33 by 16 inches for small legs. When the large bag unit is inflated after being secured in position on the leg of a patient, it has a diameter of about 9 inches, thereby forming a chamber in the bag unit around the patient's leg for treatment gas circulation.

The bag unit 20 is normally applied to a patient's leg with the two halves of the manifold facing the sides of the leg and with the zipper 37 open until the rim 20a of the open end of the bag is positioned at an appropriate location, usually at a site on the thigh. Then as indicated in FIG. 7, the rim portion at the open end is secured and sealed by suitable surgical tape 40 to the patient's skin. The tape preferably over laps the skin about an inch and is applied so as to follow the notches 34 as indicated in FIG. 7. The notches 34 are made large enough to provide a gap 34a having a width of at least about two inches between the tape sections at the mouth of the notches. This arrangement prevents any tendency for the bag and tape to have a tourniquet effect on the leg circulation. In taping the bag to the patient normally there is excess bag material to be contended with resulting from the open end of the bag being larger in circumference than the patient's limb to which the bag is being applied. This excess material is preferably externally pleated at one or more locations.

Alternatively, or in conjunction with notches 34, the rim of the open end of the bag may be cut on the bias 20a' relative to the length of the bag as indicated in FIG. 8 to prevent a tourniquet effect. Preferably the bias angle is between 45 and 70 degrees from the longitudinal axis of the bag.

With the bag unit in operating position on a patient, the supply port 24 and discharge ports 25-26 are connected to supply and discharge hoses, and the access ports 27-28 may be connected to sensors and instruments for indicating temperature, pressure, humidity and oxygen content. Pressurized oxygen or other treatment gas is supplied to the port 24 from a control and conditioning console and enters the manifold 22 comprising the space between the manifold blank 36 and the bag blank 30. The gas passes from the manifold through the holes 32 into the interior of the bag and exits the bag through the discharge ports 25, 26. The treatment gas entering the bag is preferably filtered and temperature and humidity controlled. The discharge ports are preferably connected to an outlet valve functioning to control the pressure within the bag.

Figure 11:
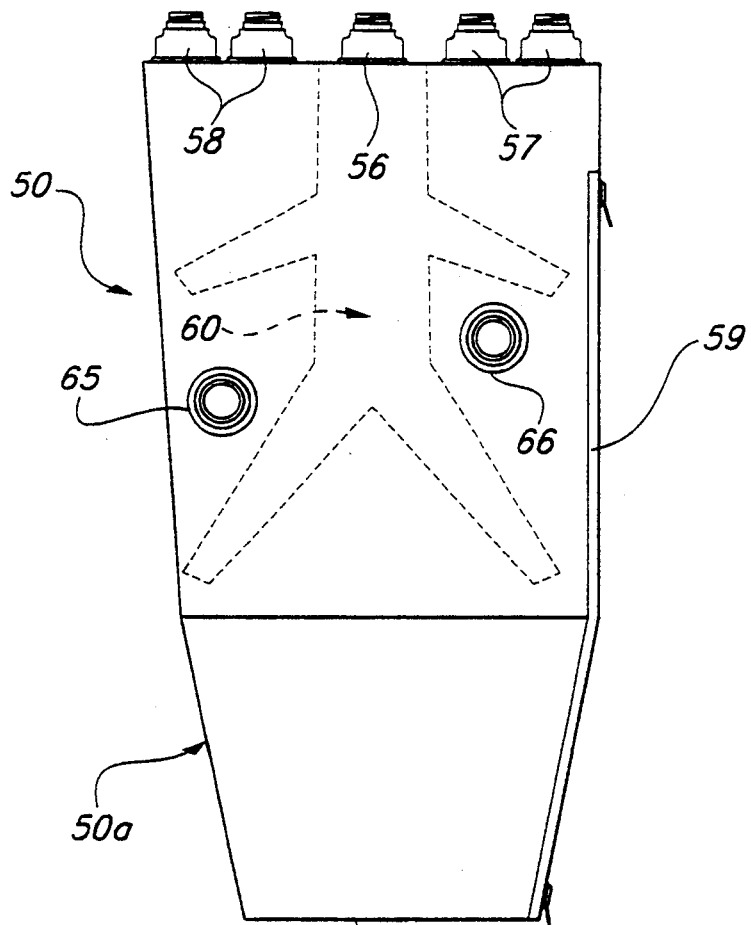
FIG. 11 is a plan view of the completed second embodiment.

Rather than having various sizes of bag units for use with various patient leg lengths and diameters, a bag may be provided that is long enough and wide enough to accommodate most patient's legs, and has a tapered section adjoining the open end of the bag. This is illustrated in a second embodiment 50 of the invention (FIG. 11) which also incorporates a modified supply manifold. To elaborate, the bag unit 50 is formed from a PVC blank 51 (FIG. 9) having a central section 52 with a straight longitudinal edge 52a and two sloped longitudinal edges 52b, 52c, at the opposite side. The ends of the blanks comprise a pair of trapezoidal apron sections 53-53' joined to the central section 52 at welded seams 54-54'. Across the center of the blank 51 there are provided a central supply port fitting 56 located between two pairs of discharge port fittings 57—57 and 58—58 surrounding port holes 56', 57' and 58' in the blank. The blank 51 may have an overall length of 120 inches and the trapezoidal end sections may each have a height lengthwise of the blank of 18 inches, and widths of 18" and 14" at the ends of the central section 52 and ends of the blank 51, respectively.

Referring to FIG. 10, mounted by peripheral welding on the reverse face of the blank 51 from the ports 56-58 is a manifold blank 60 having a central body section 60a, a head section 60b, and tapered limbs in the form of a pair of sloping tapered arm sections 60c, and a pair of diverging tapered leg sections 60d. The head section 60b overlies the central supply port 56. The outer ends of the arm sections and leg sections 60d are not secured to the blank 51 so as to provide pairs of supply jets 61-62 discharging into the bag from the intake manifold space between the blanks 51, 60 through the tapered passages defined by the tapered manifold limbs 60c-60d when the manifold is supplied with gas through the supply port fitting 56.

Complementing zipper track sections 59a, 59b for a zipper 59 like zipper 37 are attached along longitudinal side edge portions of the blank 51 as in the first embodiment. The blank 51 is folded over on itself with the manifold blank 60 on the inside, and the bag 50 is completed by welding the overlapping longitudinal side edge portions 52b-52c together. The outer ends of the trapezoidal sections 53, 53' are unattached. The resulting structure is a bag having a frustoconical open end section 50a if inflated. This section may be trimmed shorter in length at its outer end 50b to adjust for different thigh diameters and is either cut at a sloped bias or notched as previously described relative to the first embodiment to prevent a tourniquet effect when taped to the patient.

Since smooth PVC fabric tends to adhere to skin surfaces it is preferred to make the likely skin contact surfaces of the bag unit with textured PVC such as "taffeta" PVC marketed by the Maclin Company, a subsidiary of Teknor Apex Company, Industry, California. Accordingly, a rectangular platform section 63 of textured PVC is added as an extra ply over the inside face of the blank 51 endwise of the manifold section 60 and the apron sections 53–53' are made of textured PVC.

When the bag unit 50 is in use on a leg the patient's thigh is positioned over the platform section 63 and the manifold section overlies the leg. The outer trimmed edge portion of the tapered apron is taped to the patient as before. Oxygen or other treatment gas is introduced to the bag through the supply port 56, fills the delivery manifold and jets from the ends 61–62 of the tapered branches of the manifold formed between the arm and leg sections 60c–60d and the blank 51 to distribute the treatment gas. Supplemental central delivery holes 64 may be provided in the manifold. The treatment gas is discharged from the bag unit through selected ones of the discharge ports 57–58. Access ports 65–66 for monitoring can be provided as desired.

The isolator bag of the present invention has been described with reference to leg use. It will be appreciated that the invention is also applicable to isolator bags for arm use.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolator bag unit comprising:
   a flexible bag having a closed end, an open end, and a discharge port,
   said bag being adapted to loosely surround part of the length of a patient's limb starting beyond the extremity of the limb, and being adapted to be attached by adhesive adjacent its open end to the limb such that a treatment chamber is provided between the bag and the limb; and
   a flexible manifold section secured to said bag in overlapping relation to collectively with the bag provide an intake manifold chamber therebetween, said manifold chamber having an infeed port exposed outside the bag and having multiple inlet openings exposed to the interior of the bag for introducing a therapeutic gas to the interior of said treatment chamber at multiple locations for circulating in said treatment chamber and discharging therefrom through said discharge port.

2. An isolator bag unit according to claim 1 in which said bag and manifold section are formed from thin polyvinylchloride material.

3. An isolator bag unit according to claim 1 in which said manifold section is located outside of said bag, and in which said infeed port is formed in said manifold section and said inlet openings are formed in said bag.

4. An isolator bag unit according to claim 1 in which said manifold section is located inside said bag and has a border connected to the bag, and in which said infeed port is formed in said bag and said inlet openings to said treatment chamber are formed between said bag and said manifold section at portions of said border.

5. An isolator bag unit according to claim 4 in which said manifold section and bag collectively provide passages to said inlet openings from said intake manifold chamber.

6. An isolator bag unit according to claim 4 in which said passages taper toward said inlet openings.

7. An isolator bag unit according to claim 1 in which said manifold section and manifold chamber extend along opposite sides of said bag and around the closed end of said bag, and said inlet openings are located on both of said opposite sides, said infeed port being located adjacent the closed end of the bag.

8. An isolator bag unit according to claim 1 in which said manifold section extends inside the bag from the closed end of the bag along a top side of the bag, and said manifold section and bag collectively provide tapered passages from said manifold chamber to said inlet openings.

9. An isolator bag unit according to claim 8 in which said passages extend toward opposite sides of said bag.

10. An isolator bag unit according to claim 8 in which said infeed port is located adjacent said closed end of the bag, and said passages slope from said manifold chamber away from said closed end toward opposite sides of said bag.

11. An isolator bag unit according to claim 1 in which a zipper type closure operated by a slide element extends along part of the length of said bag for selectively providing access to said treatment chamber.

12. An isolator bag unit according to claim 1 in which a zipper type closure extends from the open end of the bag part way along its length, said closure being operated from either end by slide elements whereby the bag can be initially opened wider to assist in applying the bag to a patient and whereby the bag can be partly opened after application to the patient to gain access to the treatment chamber.

13. An isolator bag unit according to claim 1 in which said open end of the bag extends on a bias at an acute angle relative to the length of the bag.

14. An isolator bag unit according to claim 1 in which the rim of said open end is formed with a generally vee-shaped notch.

* * * * *